United States Patent [19]
Akhavan-Tafti et al.

[11] Patent Number: 5,883,287
[45] Date of Patent: Mar. 16, 1999

[54] VINYL SULFIDE COMPOUNDS AND A PROCESS FOR THEIR PREPARATION

[75] Inventors: Hashem Akhavan-Tafti, Brighton; Zahra Arghavani, Farmington Hills; Robert A. Eickholt, Troy, all of Mich.

[73] Assignee: Lumigen, Inc., Southfield, Mich.

[21] Appl. No.: 981,448

[22] PCT Filed: Jun. 19, 1996

[86] PCT No.: PCT/US96/09249

§ 371 Date: Dec. 22, 1997

§ 102(e) Date: Dec. 22, 1997

[87] PCT Pub. No.: WO97/00849

PCT Pub. Date: Jan. 9, 1997

Related U.S. Application Data

[63] Continuation-in-part of Ser. No. 492,715, Jun. 20, 1995, abandoned.

[51] Int. Cl.$^6$ ................................................ C07C 69/00
[52] U.S. Cl. ............................................. 560/140; 568/52
[58] Field of Search ................................ 560/140; 568/52

[56] References Cited

U.S. PATENT DOCUMENTS 5,068,339  11/1991  Scapp et al. .
5,220,005   6/1993  Bronstein .

OTHER PUBLICATIONS

Kitamura Vinylidenecyclohexadienone Acetals as Precursors of Arylvinyl Cations, Journal of Americal Chemical Society 1990, 112, 6149–6150 American Chemical Society (Kitamura 1).

Kitamura Photolysis of Vinyl Halides, Journal of Organic Chemistry 1990, 55, 1801–1805 American Chemical Society (Kitamura 2).

Kitamura Phenylthiolation of Arylvinyl Bromides by Photolysis, Journal of Organic Chemistry 1991, 56, 3739–3741 American Chemical Society (Kitamura 3).

Wladislaw New perspective for the synthetic application of some alpha–sulfenylated benzylic sulfones, synthesis of vinyl sulfides Chemical Abstracts, 122, 23, 5 Jun. 1995 Columbus, OH.

*Primary Examiner*—Samuel Barts
*Attorney, Agent, or Firm*—Richard S. Handley

[57] ABSTRACT

Vinyl sulfides bearing protected arlyoxy substituents and a process for their preparation are provided. In the process a vinyl sulfide is formed by coupling a ketone compound and a thioester compound with a low valent titanium reagent to form both carbon-carbon bonds in the same step. The vinyl sulfide compounds are useful as intermediates which are convertible into triggerable sulfur-substituted dioxetanes by addition of oxygen to the double bond. The sulfur-substituted dioxetanes additionally are useful for producing chemiluminescence or for further conversion into triggerable alkoxy, alkenyloxy, alkynloxy, aryloxy, aralkyloxy, or acyloxy-substituted dioxetanes. Triggerable dioxetanes are useful for producing chemiluminescence and in detecting activating agents in assays such as immunoassays and nucleic acid hybridization assays.

15 Claims, No Drawings

VINYL SULFIDE COMPOUNDS AND A PROCESS FOR THEIR PREPARATION

CROSS REFERENCE TO RELATED APPLICATION

This application is a continuation-in-part of applicant's U.S. application Ser. No. 08/492,715 filed on Jun. 20, 1995 now abandoned.

This is a 371 of PCT/US96/09249 filed Jun. 19, 1996.

BACKGROUND OF THE INVENTION (1). Field of the Invention

The present invention relates to a novel process for the preparation of stable chemiluminescent 1,2-dioxetane compounds which can be triggered to generate light. Stable, triggerable dioxetanes prepared by the present process are preferably of the formula:

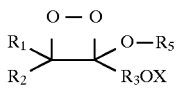

The present invention also relates to novel sulfur-substituted alkenes (vinyl sulfides) preferably of the formula:

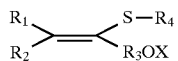

and stable triggerable sulfur-substituted 1,2-dioxetanes preferably of the formula:

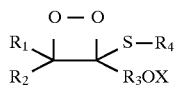

a process for their preparation and a process for their use as intermediates for producing stable triggerable 1,2-dioxetanes substituted on the dioxetane ring with alkoxy, alkenyloxy, alkynyloxy, aryloxy, aralkyloxy or acyloxy groups.

(2). Description of Related Art a. Synthesis of Dioxetanes. The preparation of dioxetanes with alkoxy substituents by addition of singlet oxygen to a vinyl ether is well known in the art. Singlet oxygen is typically produced by irradiation of a photosensitizing dye in the presence of oxygen but can also be generated by thermolysis of triphenylphosphite ozonide. Other methods of preparing dioxetanes with alkoxy substituents from vinyl ethers include electron-transfer oxidation with oxygen and triarylaminium cation radical salts (R. Curci, L. Lopez, L. Troisi, S. M. K. Rashid and A. P. Schaap, *Tetrahedron Lett.* 28, 5319–22 (1987); L. Lopez, L. Troisi and G. Mele, *Tetrahedron Lett.* 32, 117–20 (1991)), oxidation by Cr(VI) or Mo(VI) oxide diperoxides (R. Curci, L. Lopez, L. Troisi, S. M. K. Rashid and A. P. Schaap, *Tetrahedron Lett.* 29, 3145–8 (1988)) and oxidation with triethylsilyl hydrotrioxide (G. H. Posner, K. S. Webb, W. M. Nelson, T. Kishimoto and H. H. Seliger, *J. Org. Chem.*, 54, 3252–4 (1989)). A dioxetane was produced in low yield by reaction of a dioxene compound with oxygen which had been passed through an electric discharge, apparently producing a small amount of singlet oxygen in addition to ozone (T.-S. Fang and W.-P. Mei, *Tetrahedron Lett.* 28, 329–21 (1987)).

All of these methods for the preparation of alkoxy-substituted dioxetanes require the preparation of the precursor vinyl ether. No reaction involving the direct introduction of alkoxy or aryloxy groups on a pre-formed dioxetane ring has been reported to the best of applicant's knowledge. There is thus a need for a general method for the preparation of a variety of alkoxy-substituted dioxetanes from a common intermediate which does not require the preparation of each individual vinyl ether precursor.

b. Sulfur-Substituted Dioxetanes. 1,2-Dioxetanes with one or more sulfur-containing substituents on the dioxetane ring are known. All known examples are unstable, with most decomposing rapidly at room temperature. (W. Adam, L. A. Arias, D. Scheutzow, *Tetrahedron Lett.*, 23(28), 2835–6 (1982); W. Adam, L. A. Encarnacion, *Chem. Ber.*, 115(7), 2592–605 (1982); W. Ando, K. Watanabe, T. Migita, *J. Chem. Soc., Chem. Commun.* (24), 961–2 (1975); G. Geller, C. S. Foote, D. B. Pechmann, *Tetrahedron Lett.* 673–6 (1983); R. S. Handley, A. J. Stern, A. P. Schaap, *Tetrahedron Lett.* 26, 3183–6 (1985)). The most stable sulfur-substituted dioxetanes, derived from 4,5-dialkyl-2,3-dihydrothiophene decompose with a half-life of a few minutes at room temperature (W. Adam, A. Griesbeck, K. Gollnick, K. Knutzen-Mies, *J. Org. Chem.*, 53, 1492–5 (1988); K. Gollnick, K. Knutzen-Mies, *J. Org. Chem.*, 56, 4027–31 (1991)). Two spiroadamantyl-substituted dioxetanes bearing one and two sulfur substituents, respectively, on the dioxetane ring are known. Both have been reported to rapidly and completely decompose on attempted isolation at room temperature (W. Adam, L. A. Encarnacion, *Chem. Ber.*, 115(7), 2592–605 (1982)).

c. Synthesis of Vinyl Sulfides. Vinyl sulfides containing a carbon-carbon double bond and a sulfur substituent directly attached to one of the double bond carbon atoms can be prepared by various methods known to the skilled synthetic chemist. One of the classical methods for preparation of vinyl sulfides involves the reaction of a ketone and mercaptan with TiCl$_4$ and an amine base (T. Mukaiyama, K. Saigo, Chem. Lett., 479–82, 1973)). vinyl sulfides have been formed by other methods which utilize titanium reagents. Vinyl sulfones are reduced at the sulfur to vinyl sulfides with LiAlH$_4$-TiCl$_4$ (E. Akgun, K. Mahmood, C. A. Mathis, *J. Chem. Soc., Chem. Commun*, (6), 761–2 (1994)). α-Halosulfoxides undergo elimination and reduction with Zn-TiCl$_4$ to form vinyl sulfides (V. Retrakul, P. Poochaivatananon, *Tetrahedron Lett.*, 24(5), 531–4 (1983)). In each of these methods, one or both of the C—C bonds is already formed in the starting material. None of the foregoing methods involves the direct formation of the sulfur-substituted carbon-carbon double bond from two separate carbon atoms. No method of which Applicants are aware is known for creating a vinyl sulfide by coupling two carbonyl-containing compounds, one of which is a thioester, to form a double bond with a sulfur-substituent.

d. Chemically Triagerable Dioxetanes. Chemically triggerable adamantyl-stabilized dioxetanes are disclosed in U.S. Pat. No. 4,857,652 and a paper (A. P. Schaap, T. S. Chen, R. S. Handley, R. DeSilva, and B. P. Giri, *Tetrahedron Lett.*, 1155 (1987)). These dioxetanes exhibit thermal half-lives of years but can be triggered to produce efficient chemiluminescence on demand. Benzofuranyl dioxetanes substituted with trialkylsilyl and acetyl-protected phenolic groups which produce weak chemiluminescence have also been reported (W. Adam, R. Fell, M. H. Schulz, *Tetrahedron*, 49 (11), 2227–38 (1993) ; W. Adam, M. H. Schulz, *Chem. Ber.*, 125, 2455–61 (1992)). Each of these dioxetanes was prepared by dye-sensitized photooxygenation of a vinyl ether (alkene) precursor.

e. Enzymnatically TPriacrrablp Dioxetanes. Enzymatic triggering of adamantyl-stabilized 1,2-dioxetanes are described in U.S. Pat. No. 4,857,652 and a series of papers (A. P. Schaap, R. S. Handley, and B. P. Gini, *Tetrahedron Lett.*, 935 (1987); A. P. Schaap, M. D. Sandison, and R. S. Handley, *Tetrahedron Lett.*, 1159 (1987) and A. P. Schaap, Photochemn. Photobiol., 47S, 50S (1988)). These dioxetanes bear a protected aryloxide substituent which is triggered to decompose with emission of light by the action of an enzyme in an alkaline aqueous buffer to give an aryloxide intermediate dioxetane which decomposes with emission of light at a greatly increased rate. Chemiluminescence is thereby emitted at a much greater intensity than that resulting from slow thermal decomposition of the protected form of the dioxetane. Further examples of enzymatically triggered dioxetanes are disclosed in U.S. Pat. No. 5,068,339 to Schaap, U.S. Pat. Nos. 5,112,960 and 5,220,005 and a PCT application (88 00695) to Bronstein, U.S. Pat. No. 4,952,707 to Edwards, U.S. Pat. No. 5,132,204 to Urdea, U.S. Pat. No. 5,248,618 to Haces and PCT application WO94/10258 to Wang and in a publication (M. Ryan, J. C. Huang, O. H. Griffith, J. F. Keana, J. J. Volwerk, *Anal. Biochem.*, 214(2), 548–56 (1993)). The enzymatically triggerable dioxetanes are now undergoing widespread use as substrates for marker enzymes in numerous applications including immunoassays, gene expression studies, Western blotting, Southern blotting, DNA sequencing and the identification of nucleic acid segments in infectious agents.

New processes for the-preparation of existing and new triggerable dioxetanes. are desirable -to advance the state of the art. Processes which permit the preparation of dioxetane compounds which are difficult or impossible to prepare by known methods would be particularly desirable. The process of the present invention provides such means.

OBJECTS

It is an object of the present invention to provide novel aryl group-substituted 1,2-dioxetanes further substituted on the dioxetane ring with a thioalkyl or thioaryl group $SR_4$. It is an object of the present invention to provide novel aryl group-substituted vinyl sulfides and a process for their preparation, said vinyl sulfides being used in preparing the sulfur-substituted dioxetanes. It is a further object of the present invention to provide a process for producing stable 1,2-dioxetanes by replacement of the sulfur-containing group $SR_4$ of a sulfur-substituted dioxetane with an alkoxy, alkenyloxy, alkynyloxy, aryloxy, aralkyloxy or acyloxy group $OR_5$. It is also an object of the present invention to provide a process of preparation of stable 1,2-dioxetanes containing an alkoxy, alkenyloxy, alkynyloxy, aryloxy, aralkyloxy or acyloxy group $OR_5$ and further substituted on the dioxetane ring with aryl group substituted with an OX substituent which can be triggered by activating agents to remove a protecting group X and consequently generate chemiluminescence. It is a further object of the present invention to provide a general process for producing a number of different stable 1,2-dioxetanes each substituted on the dioxetane ring with different alkoxy, alkenyloxy, alkynyloxy, aryloxy, aralkyloxy or acyloxy groups $OR_5$ by replacement of the sulfur-containing group $SR_4$ of a sulfur-substituted dioxetane.

Dioxetane compounds prepared by the process of the present invention can be used in assay methods to signal the presence or amount of an analyte, in emergency and novelty lighting applications and as light standards for luminometer calibration. Dioxetane compounds which are triggered by an activating agent to produce light are useful in immunoassays and the detection of nucleic acids, antibodies, haptens and antigens by generally known methods.

DESCRIPTION OF THE PREFERRED EMBODIMENTS

The present invention relates to a general process for the preparation of stable aryl group-substituted 1,2-dioxetanes (III) further substituted on the dioxetane ring with an alkoxy, aryloxy or acyloxy group which dioxetane can be triggered to generate chemiluminescence. The process involves the substitution of an alkoxy, alkenyloxy, alkynyloxy, aryloxy, aralkyloxy or acyloxy. group $OR_5$ for a thioalkyl or thioaryl group $SR_4$ on the dioxetane ring of a sulfur-substituted dioxetane (II) mediated by an electrophilic compound E-Y. Until Applicant's process was discovered, no process existed which was generally applicable to the preparation of a series of stable dioxetanes from a common intermediate; each dioxetane was prepared by addition of oxygen to the independently prepared alkene precursor. The success of the present process resides in the unanticipated discovery that certain sulfur-substituted dioxetanes can react with hydroxyl group-containing compounds in the presence of an electrophile to rep lace the-sulfur substituent with an alkoxy, alkenyloxy, alkynyloxy, aryloxy, aralkyloxy or acyloxy group $OR_5$.

Sulfur-substituted dioxetanes of the present invention are prepared by addition of oxygen to a vinyl sulfide (I). The sequence of reactions is shown in the Scheme below.

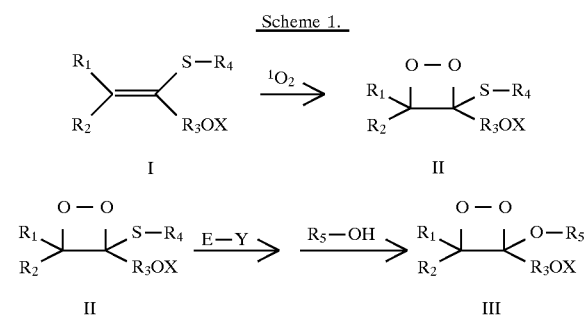

While not wishing to be bound by any particular theory, a plausible explanation for the reaction is illustrated in the Scheme shown below.

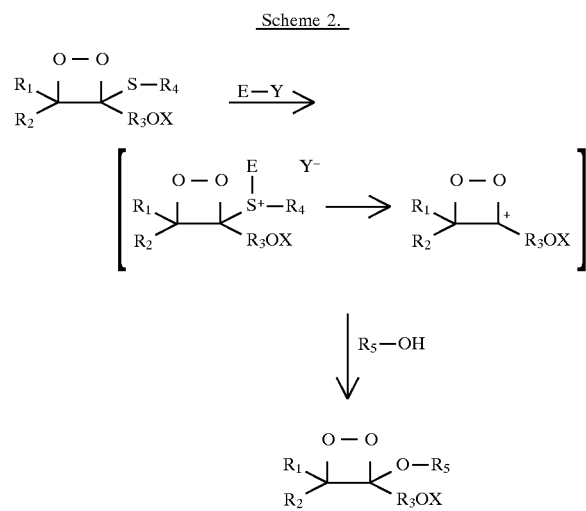

No reaction involving the direct substitution of groups on a dioxetane ring has ever been reported. The present invention represents the first demonstration of the synthesis of a dioxetane by replacing one of the dioxetane ring substituents of a different precursor dioxetane. The ability to selectively replace one of the ring substituents readily allows the synthesis of a variety of new dioxetane compounds from a common intermediate.

Sulfur-substituted dioxetanes useful in practicing the process of the present invention can be of the formula:

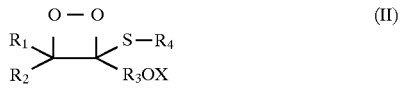

(II)

wherein $R_1$ and $R_2$ are organic groups providing sufficient stability to the dioxetane to permit conversion to an alkoxy, alkenyloxy, alkynyloxy, aryloxy, aralkyloxy or acyloxy-substituted dioxetane. The groups $R_1$ and $R_2$ are chosen from branched chain or cyclic alkyl, substituted alkyl or heteroalkyl groups. $R_1$ and $R_2$ can optionally be joined together to form a cyclic or polycyclic group which is spiro-fused to the dioxetane ring. The group $R_4$ is selected from $(C_1-C_{20})$ alkyl, $(C_7-C_{30})$ aralkyl and $(C_6-C_{30})$ aryl groups which can optionally contain non-interfering substituents and optionally contain N, O, S, P or halogen heteroatoms within the alkyl, aralkyl or aryl group. The group $R_3$ is selected from aryl, biaryl, heteroaryl, fused ring polycyclic aryl or heteroaryl groups in which one or more of the ring hydrogens can be replaced by an atom or group selected from halogens, alkyl, alkoxy, substituted alkoxy, carbonyl, carboxyl, amino and alkylamino groups. The X group can be any protecting group which serves to block formation of the aryloxide anion and which can be replaced or removed as desired by an activating agent to form the aryloxide anion. Representative OX groups include hydroxyl, alkoxy, substituted alkoxy (e.g. methoxyethoxymethoxy (MEM-O) and trimethylsilylethoxymethoxy (SEM-O)), acyloxy having the formula $OOCR_{10}$ wherein $R_{10}$ is selected from alkyl and aryl groups containing 2 to 20 carbon atoms, trialkylsilyloxy, triarylsilyloxy, aryldialkylsilyloxy, $OPO(OR_8)_2$ wherein $R_8$ is an organic group, oxygen pyranoside including, without limitation, β-D-galactosyloxy and β-D-glucuronidyloxy groups.

In a preferred embodiment, the process is used to form a sulfur-substituted dioxetane (V) wherein the $R_1$ and $R_2$ groups are joined together as a polycyclic alkyl group spiro-fused to the dioxetane ring as represented by the formula:

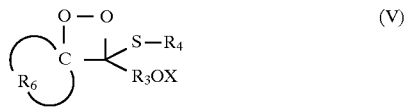

(V)

wherein

is the polycyclic alkyl group. Most preferred is a sulfur-substituted dioxetane wherein the

group is an adamantyl group with optional non-hydrogen substituents.

Electrophilic agents useful in practicing the present invention include but are not limited to halogens including $Cl_2$, $Br_2$, $I_2$, ICl and IBr, hydrogen peroxide, singlet oxygen, pseudo-halogens such as N-chlorosuccinimide (NCS), N-bromosuccinimide (NBS) and N-iodosuccinimide (NIS), alkylating agents including alkyl halides and alkyl sulfates and sulfonates, transition metal salts, especially salts of mercury, silver and gold, and Lewis acids such as titanium tetrachloride. In one embodiment, the compound of structure E-Y may serve as both the electrophilic agent and the hydroxylic compound $R_5O^-M^+$. Compounds of this type described generically as $(R_5O^-)_nM^{+n}$ wherein M is a metal with a strong propensity to react with sulfur, such as silver, gold and especially, mercury, wherein n is 1,2 or 3 and wherein $R_5O^-$ is an anion of a hydroxylic compound, in particular a carboxylate anion are effective to replace the $SR_4$ group of a sulfur-substituted dioxetane with an $OR_5$ group. A preferred compound of this type is mercuric acetate $Hg(OAc)_2$.

Photosensitizers useful in practicing the process of the invention include compounds known in the art to produce singlet oxygen upon irradiation with visible light in the presence of ground state oxygen. Exemplary photosensitizers include methylene blue, Rose Bengal, eosin, erythrosin, rhodamines, porphyrins, metal porphyrins and fullerenes. Photosensitizers may be employed as the soluble dye or linked to an insoluble support such as silica or a polymer bead. Preferred photosensitizers are methylene blue or polymer-bound Rose Bengal.

In a preferred mode of carrying out the inventive process, a vinyl sulfide containing a sulfur substituent $SR_4$, wherein $R_4$ is an organic group containing 1 to 20 carbon atoms and optionally heteroatoms is converted by low temperature photooxygenation to the corresponding sulfur-substituted 1,2-dioxetane by addition of singlet oxygen to the double bond. Progress of this reaction is readily monitored by thin layer chromatography (TLC) or $^1H$ NMR by observing the disappearance of the vinyl sulfide. Additionally, heating a small portion of the reaction solution leads to easily detectable chemiluminescence indicating formation of the sulfur-substituted dioxetane. Visualization of the sulfur-substituted dioxetane by triggering with fluoride in DMSO produces yellow-greenish chemiluminescence which is discernible to the unaided eye. Sulfur-substituted dioxetane compounds of relatively lower thermal stability are preferably not isolated at this point but instead directly reacted at a low temperature with a compound containing a hydroxyl group or a salt thereof. Sulfur-substituted dioxetane compounds of relatively higher thermal stability can be first isolated before reaction with a compound containing a hydroxyl group or a salt thereof. An electrophilic compound is added at low temperature to the sulfur-substituted dioxetane in an amount ranging from about 0.5 mol to about 1.5 mol of electrophilic compound per mol of dioxetane based on complete conversion of the vinyl sulfide. It is especially preferred that the photooxygenation and addition of electrophilic compound be performed at or below about −40° C.; use of a Dry Ice-isopropyl alcohol mixture, ca. −78° C., for cooling is particularly suited for this purpose. A hydroxylic compound $R_5$—OH selected from alcohols, phenols where phenols are defined as aryl ring compounds with at least one OH substituent and carboxylic acids or their salts, if not already present as the reaction solvent, is added at low temperature in an amount of at least about 1 mol to 2 mol per mol .of the vinyl sulfide. The hydroxylic compound is permitted to react with the dioxetane to effect replacement of the $SR_4$ group with the $OR_5$ group.

Vinyl sulfide compounds (I) useful in practicing the present invention are preferably of the formula:

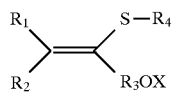

wherein $R_1$ and $R_2$ are organic groups which can optionally be joined together to form cyclic or polycyclic groups, wherein $R_4$ is selected from $(C_1-C_{20})$ alkyl, $(C_7-C_{30})$ aralkyl and $(C_6-C_{30})$ aryl groups and optionally containing heteroatoms, wherein $R_3$ is selected from aryl, biaryl, heteroaryl, fused ring polycyclic aryl or heteroaryl groups which can optionally contain non-interfering substituents and wherein X is a protecting group. Preferred $R_1$ and $R_2$ groups are selected from branched chain alkyl, cycloalkyl and aryl groups containing 3 to 20 carbon atoms and optionally heteroatoms.

In a preferred embodiment, a vinyl sulfide having the formula:

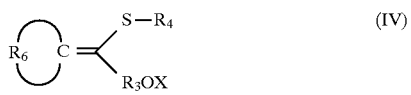

is used wherein

is selected from cyclic and polycyclic organic groups which can optionally be substituted. It is preferred that $R_3$ is an optionally substituted phenyl, naphthyl or other fused-ring aryl group. It is especially preferred that $R_3$ is a phenyl group in which an OX group is oriented meta to the dioxetane ring group as shown below. The phenyl ring can optionally contain additional ring substituents independently selected from halogens, alkyl, substituted alkyl, alkoxy, substituted alkoxy, carbonyl, carboxyl, amino and alkylamino groups. The group

is more preferably a polycyclic group, preferably an adamantyl group optionally having one or more non-interfering substituent groups selected from halogens, alkyl, substituted alkyl, alkoxy, substituted alkoxy, carbonyl, carboxyl, phenyl, substituted phenyl, amino and alkylamino groups covalently bonded thereto. Vinyl sulfides useful in practicing the process of the present invention can be prepared by art-known methods for the preparation of vinyl sulfides. An exemplary process for the preparation of vinyl sulfides is disclosed in T. Mukaiyama, K, Saigo, Chem. Lett., 479–82 (1973).

In another embodiment of the present invention, vinyl sulfide (IV) is formed by coupling a ketone compound and a thioester compound with a low valent titanium reagent exemplified by the following reaction:

Scheme 3.

This reaction process achieves the direct formation of both carbon-carbon bonds of the vinyl sulfide product. The low valent titanium reagent, which is used in excess, is prepared by reacting a titanium salt, preferably $TiCl_3$ or $TiCl_4$ with a metallic reducing agent selected from lithium, sodium, potassium, zinc and zinc-copper alloys or a metal hydride including, without limitation, sodium hydride, potassium hydride, aluminum hydride, lithium aluminum hydride or potassium triethylborohydride in the presence or absence of an amine base in an aprotic solvent, preferably tetrahydrofuran. The ratio of ketone to thioester is preferably from about 1:3 to about 3:1. The reaction between the ketone and thioester is conducted between about 0° C. and the reflux temperature of the solvent, preferably between about 20° C. and about 70° C.

Thioalkyl- and thioaryl-substituted dioxetanes of the present invention are surprisingly stable and can be manipulated at temperatures of –10° to 25° C. Reaction of the thioalkyl- and thioaryl-substituted dioxetanes of the present invention with an activating agent to cleave the O—X bond and remove the X group yields an unstable oxide intermediate dioxetane compound is formed which decomposes and releases electronic energy to form light and two carbonyl-containing compounds of the formula:

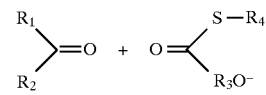

In contrast, all dioxetanes bearing sulfur substituents known in the prior art including those with an adamantyl substituent, spontaneously decompose at or, in most cases, well below room temperature. It was particularly-unexpected that a sulfur-substituted dioxetane would exhibit decay rates in alkaline amine buffers containing metal salts comparable to analogous alkoxy-substituted dioxetanes.

Stable alkoxy, alkenyloxy, alkynyloxy, aryloxy, aralkyloxy or acyloxy-substituted dioxetanes which can be prepared by the process of the present invention are of the formula:

wherein $R_1$ and $R_2$ are organic groups which provide stability and which can optionally be joined together to form a cyclic or polycyclic group which is spiro-fused to the dioxetane ring, wherein $R_5$ is selected independently from the group consisting of $(C_1-C_{20})$ alkyl groups, $(C_2-C_{20})$ alkenyl groups, $(C_2-C_{20})$ alkynyl groups, $(C_6-C_{30})$ aryl groups, $(C_7-C_{30})$ aralkyl groups and $(C_1-C_{20})$ acyl groups. $R_5$ can optionally be substituted with one or more substituents including, without limitation, hydroxy, alkoxy, halogen, cyano, nitro, amino, imine, ketone, aldehyde, carboxylic acid, carboxylic ester, carboxamide, thiol, thioester, trialkylsilyloxy, triarylsilyloxy and alkyldiarylsilyloxy substituents. The group $R_3$ is selected from aryl, biaryl, heteroaryl, fused ring polycyclic aryl and fused ring polycyclic heteroaryl groups which can optionally be substituted with non-interfering groups. X is a group which can be removed by an activating agent as is generally known in the art to form an unstable oxide intermediate dioxetane compound. In another embodiment, X can be a group such as a hydrogen atom or a labile group which can be replaced with another removable group without triggering the decomposition of the dioxetane. Representative OX groups include hydroxyl, alkoxy, substituted alkoxy (e.g. methoxyethoxymethqxy (MEM-O) and trimethylsilylethoxymethoxy (SEM-O)), acyloxy having the formula $OOCR_{10}$ wherein $R_{10}$ is selected from alkyl and aryl groups containing 2 to 20 carbon atoms, trialkylsilyloxy, triarylsilyloxy, aryldialkylsilyloxy, $OPO(OR_8)_2$ wherein $R_8$ is an organic group, $OPO_3^{2-}$ salts and oxygen pyranoside including, without limitation, β-D-galactosyloxy and β-D-glucuronidyloxy groups.

When chemiluminescence is to be generated the stable dioxetane is triggered with an activating agent to generate an unstable oxide intermediate dioxetane which decomposes and releases electronic energy to form light and two carbonyl containing compounds as shown in Scheme 4 below.

Scheme 4.

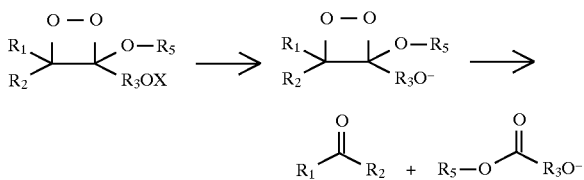

A preferred dioxetane compound which can be made by the process of the present invention is a stable dioxetane of the formula:

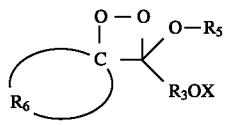

wherein

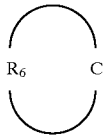

is selected from cyclic and polycyclic organic groups, which can optionally be substituted with non-interfering groups and which is spiro-fused to the dioxetane ring and which provides thermal stability, wherein $R_3$, $R_5$ and X are as defined above so that when the dioxetane is triggered to remove the X group by an activating agent an unstable oxide intermediate dioxetane compound is formed which decomposes and releases electronic energy to form light and two carbonyl-containing compounds of the formula:

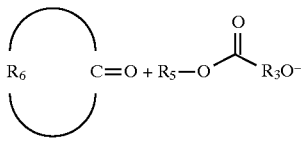

In a preferred embodiment, the group

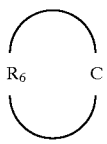

is a polycyclic organic group spiro-fused to the dioxetane ring, containing 6 to 30 carbon atoms and which can optionally be substituted with non-interfering groups and which provides thermal stability. The group

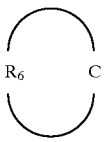

is more preferably an adamantyl group optionally having at least one substituent group selected from halogens, alkyl, substituted alkyl, alkoxy, substituted alkoxy, carbonyl, carboxyl, phenyl, substituted phenyl, amino and alkylamino groups covalently bonded thereto. In another preferred embodiment the group $R_3$ is a phenyl or naphthyl group. It is especially preferred that $R_3$ is a phenyl group in which the OX group as defined above is oriented meta to the dioxetane ring group as shown below. The phenyl ring can optionally contain additional ring substituents independently selected from halogens, alkyl, substituted alkyl, alkoxy, substituted alkoxy, carbonyl, carboxyl, amino and as alkylamino groups.

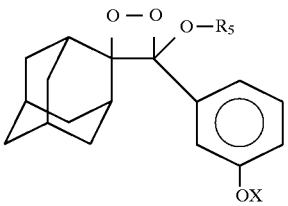

The stable 1,2-dioxetane compounds have long half-lives at room temperature, typically ≧1 year, but can be triggered by an activating agent to decompose rapidly with half-lives ranging from seconds to a few minutes depending on the microenvironment where the dioxetane is located.

Aryloxy-substituted dioxetanes of the formula:

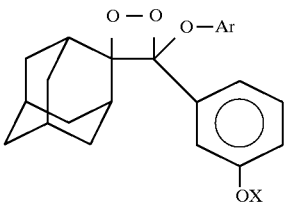

have been prepared, it is believed for the first time, by the process of the present invention by using a phenol as the hydroxylic compound $R_5OH$. Dioxetanes wherein Ar is an optionally substituted ($C_6$–$C_{30}$) aryl group and wherein X is a removable group are highly stable compounds which produce visible light when triggered to remove X.

It is contemplated that the hydroxylic compound $R_5OH$ may itself be another dioxetane molecule with a phenolic group. In this embodiment, chains of directly linked, oligomeric or polymeric dioxetanes are formed. Further, such oligomeric or polymeric dioxetanes can serve as the hydroxylic compound in order to build chain structures of greater length. A requirement for this process is that the OX group of the monomeric, oligomeric or polymeric dioxetane serving as the $R'_5OH$ component be present as OH. An example showing formation of a dimeric bis-dioxetane (VII) is illustrated below to aid in understanding the process.

Scheme 5.

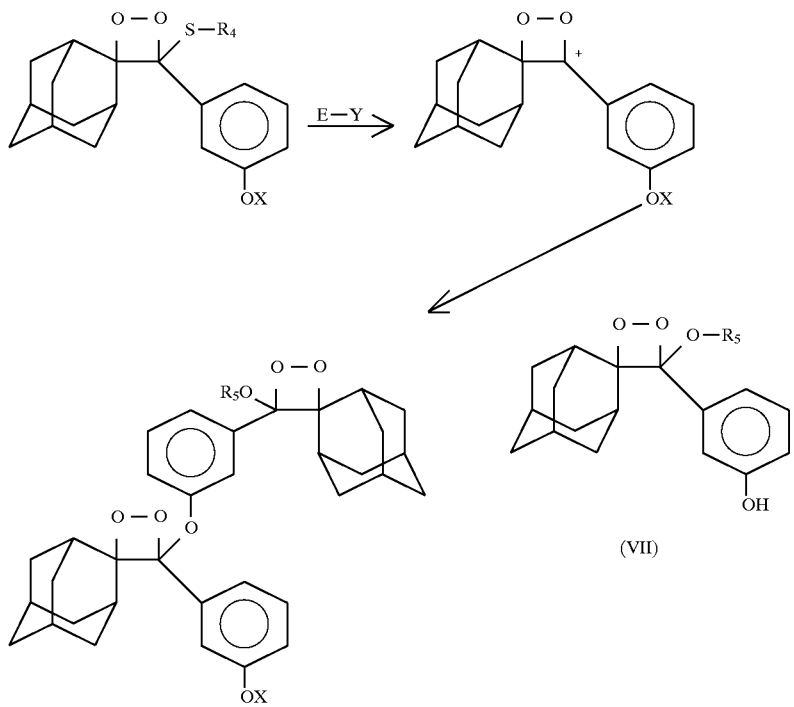

It will be obvious in view of the foregoing description that, under appropriate conditions, the intermediate carbonium ion can serve as its own $R_5OH$ component; i.e. when X is H a self-condensation can occur to produce an oligomeric or polymeric. dioxetane chain compound. A substoichiometric amount of a competing $R'_5OH$ compound is required to effect chain termination. A possible dioxetane compound (VIII) prepared by this process is illustrated to aid in understanding the process.

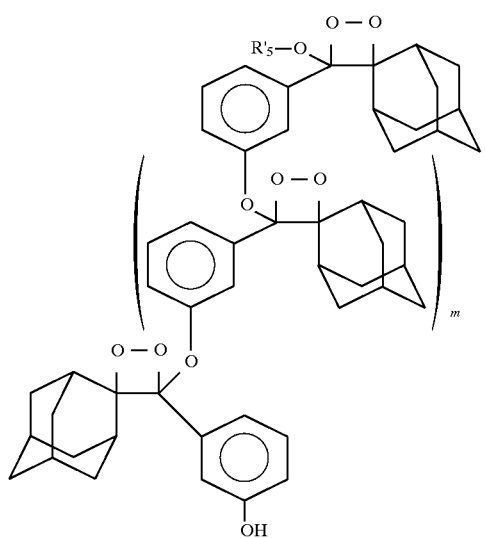

(VIII)

An acyloxy-substituted dioxetane of the formula:

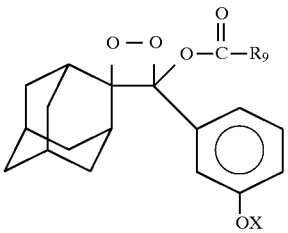

has been prepared for the first time by the present process. In preparing a dioxetane of this structure, the hydroxylic compound can be a carboxylic acid $R_9COOH$, a salt thereof or it can be as the electrophilic compound in the manner described above. Dioxetanes wherein $R_9$ is an optionally substituted ($C_1$–$C_{20}$) alkyl or aryl group and wherein X is a removable group are also stable compounds which emit light when triggered to remove X.

A significant advantage of the present process for preparing alkoxy, alkenyloxy, alkynyloxy, aryloxy, aralkyloxy or acyloxy-substituted dioxetanes is that a single vinyl sulfide precursor compound can be converted into any of a large number of other dioxetane compounds limited only by the availability of the hydroxylic compound $R_5$—OH or salt $R_5O^-M^+$. Since the $OR_5$ group is not introduced until after formation of the dioxetane ring, it is possible to prepare dioxetane compounds which would be problematic to prepare by the prior art process of photooxygenating a vinyl ether precursor. The present process is amenable to the preparation of dioxetanes with groups which could interfere with the photooxygenation either by quenching of singlet oxygen, or by quenching or bleaching the photosensitizer. The present process is also amenable to the preparation of dioxetanes with groups which make the vinyl ether more electron-deficient and therefore less reactive or unreactive to singlet oxygen. The present process further permits the preparation of dioxetanes with groups such as C—C double bonds which are themselves reactive toward singlet oxygen.

Dioxetanes prepared by the process of the present invention can be used in a process for generating light which comprises reacting an activating agent with a stable 1,2-dioxetane of the formula (III):

 (III)

wherein the X group is removed by the activating agent to form an unstable oxide intermediate dioxetane compound which decomposes and releases electronic energy to form light and two carbonyl-containing compounds of the formula:

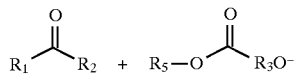

In another embodiment, the activating agent can be a chemical, including an enzyme, which reacts catalytically or stoichiometrically to trigger the dioxetane. Exemplary activating agents are disclosed, for example, in U.S. Pat. No. 4,857,652 the relevant portion of the disclosure of which is incorporated herein by reference. Activating agents which react catalytically or stoichiometrically to trigger the dioxetane by removal of the X group are well known in the art. Reactions can be conducted in aqueous solution, in which case it is often desirable to use one or more art-known chemiluminescence enhancers to increase or prolong light emission. Reactions can also be conducted in polar, aprotic solvents such as dimethyl sulfoxide, N,N-dimethylformamide or acetonitrile.

The process for generating light can be performed in solution or on the surface of a solid support such as a membrane. Dioxetanes prepared by the process of the present invention can further be incorporated into a chemiluminescent composition which comprises a dioxetane, one or more enhancer substances and optional fluorescers. Enhancers are substances which increase the amount of light produced on triggering the dioxetane. Enhancer substances well known in the art increase chemiluminescence either by providing a hydrophobic environment in which the light emitting reaction can occur or through energy transfer to a fluorescent compound held in proximity to the dioxetane.

The development of particular assays and kits using dioxetanes prepared by the process of the present invention will be readily apparent to the skilled artisan. The methods of use of the dioxetanes which can be prepared by the present process are illustrative of their utility only. The uses do not constitute a part of the invention per se.

EXAMPLES

In order to more fully describe the various aspects of the present invention, the following examples are described. The examples are to be considered illustrative and do not limit the scope of the invention.

Sulfur-substituted dioxetane compounds prepared using the process of the present invention are shown below.

TABLE 1

Dioxetane Compounds

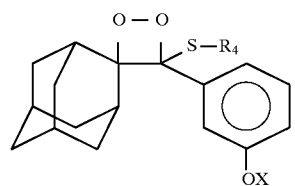

| Dioxetane | $R_4$ | OX |
|---|---|---|
| 1 | $CH_2CH_3$ | OH |
| 2 | $CH_2CH_3$ | $OOCC(CH_3)_3$ |
| 3 | $4-C_6H_4F$ | OH |
| 4 | $4-C_6H_4F$ | $OOCC(CH_3)_3$ |
| 5 | $CH_2CF_3$ | OH |

Example 1

Synthesis of Compound 1. 4-Ethylthio-4-(3-hydroxyphenyl) spiro[1,2-dioxetane-3,2'-tricyclo[3.3.1.1$^{3,7}$]decane].

(a) Synthesis of 3-hydroxyphenyl tricyclo[3.3.1.1$^{3,7}$]dec-2-yl ketone. To a stirred solution of 20.00 g (0.07397 mol) of [(3-hydroxyphenyl)methoxymethylene]tricyclo[3.3.1.1$^{3,7}$] decane (preparation described in U.S. Pat. No. 4,857,652) in 300 mL of methanol was added 5 mL of concentrated hydrochloric acid. After about fifteen minutes, a white precipitate began to form. The reaction was allowed to stir overnight. Water (500 mL) was added to the reaction mixture, and the precipitate was collected by suction filtration and washed with an additional 500 mL of water. After air drying for a few hours, the solid was dissolved in ethyl acetate and dried over magnesium sulfate. The magnesium sulfate was filtered and the ethyl acetate removed in vacuo yielding 23.42 g (97% yield) of the pure ketone as a white solid. $^1$H NMR (CDCl$_3$) δ 1.55–2.05 (m, 12H), 2.309 (br s, 2H), 3.41 (br s, 1H), 6.99–7.39 (m, 4H).

(b) Synthesis of [(3-hydroxyphenyl) ethylthiomethylene] tricyclo[3.3.1.1$^{3,7}$]decane. The ketone was converted to the vinyl sulfide by the method of Mukaiyama (T. Mukaiyama, K, Saigo, Chem. Lett., 479–82, 1973)). An argon-purged round bottom flask was charged with 10.0 g (39 mmol) of the hydroxy ketone, 250 mL of anhydrous tetrahydrofuran (THF), and 9.5 mL (2.2 eq.) of TiCl$_4$. The resulting brown solution was stirred under argon for 30 minutes at room temperature. A solution of 24.0 mL (4.4 eq.) of triethylamine (Et$_3$N) dried over KOH and 3.2 mL (1.1 eq.) of ethanethiol in 200 mL of dry THF was then added dropwise to the reaction solution over a 2 hour period while the reaction solution darkened to a deep reddish brown. Stirring was maintained overnight. A portion of dry Et$_3$N (100 mL) was added to the reaction solution causing the brief formation of some precipitate. The excess TiCl$_4$ was neutralized by the addition of methanol. This caused the formation of precipitate, turned the reaction mixture from brown to yellow to green, and caused the reaction mixture to heat up. The reaction mixture was found to still be basic by pH paper and was allowed to stir for an hour. The reaction mixture had turned back to a bright yellow color by the end of this hour. The mixture was then suction filtered and the white precipitate obtained was washed with ethyl acetate and discarded. The solvents were then removed in vacuo from the filtrate yielding a brownish yellow solid. This solid was then taken up into 500 ML of ethyl acetate and the resulting mixture washed several times with water (emulsion formed). The ethyl acetate layer was then dried over magnesium sulfate, filtered and concentrated in vacuo yielding a viscous yellow oil which smelled of thiol. The oil was chromatographed on silica gel using methylene chloride as eluent. The desired vinyl sulfide and the starting ketone were recovered. The solvents were removed in vacuo from the first eluted fraction yielding 8.57 g of light yellow oil which gradually solidified over the course of several days. $^1$H NMR (CDCl$_3$) δ 1.105 (t, 3H, J=7.3 Hz), 1.64–2.00 (m, 12H), 2.238 (q, 2H, J=7.3 Hz), 2.64 (br s, 1H), 3.58 (br s, 1H), 4.813 (s, 1H), 6.69–6.83 (m, 3H), 7.175 (t, 1H).

(c) Synthesis of 4-ethylthio-4-(3-hydroxyphenyl)spiro[1,2-dioxetane-3,2'-tricyclo[3.3.1.1$^{3,7}$]decane] (1). A small photooxygenation apparatus was charged with 102 mg of the vinyl sulfide, 1–2 mg of methylene blue, and 10 mL of methylene chloride dried over magnesium sulfate. The resulting solution was then cooled to −78° C. with oxygen bubbling through it. After several minutes, the reaction solution was irradiated with a 1000 W sodium lamp (GE LUCALOX) shielded by a 0.005" polyimide film (DuPont) for 20 min to produce the dioxetane. Mixing a sample of the dioxetane with an excess of tetrabutylammonium fluoride (TBAF) in DMSO produced yellow chemiluminescence.

Example 2 synthesis of compound 2. 4-Ethylthio-4-(3-pivaloyloxyphenyl)spiro[1,2-dioxetane-3,2'-tricyclo-[3.3.1.1$^{3,7}$]decane].

(a) Synthesis of 3-pivaloyloxyphenyl-tricyclo[3.3.1.1$^{3,7}$]-dec-2-yl ketone. 3-Hydroxyphenyl-tricyclo[3.3.1.1$^{3,7}$]dec-2-yl ketone (2.1 g, 8.2 mmol) was dissolved in 200 mL of CH$_2$Cl$_2$ and 4.6 mL of Et$_3$N (4 eq.). Pivaloyl chloride (1.1 mL, 1.1 eq.) was added dropwise to the solution and the reaction stirred for two hours to complete acylation of the phenol group. The solution was extracted with three 100 mL portions of water and dried over MgSO$_4$. Evaporation of the solvent left a colorless oil which slowly solidified. Yield 2.77 g; $^1$H NMR (CDCl$_3$) δ 1.369 (s, 9H), 1.55–2.05 (m, 12H), 2.307 (br s, 2H), 3.422 (br s, 1H), 7.20–7.68 (m, 4H).

(b) Synthesis of [(3-pivaloyloxyphenyl)ethylthiomethylene]-tricyclo[3.3.1.1$^{3,7}$]decane. An Ar-purged round bottom flask was charged with 0.50 g (1.47 mmol) of the pivaloyloxy ketone, 20 mL of dry THF, and 0.16 mL (1 eq.) of TiCl$_4$. The resulting orange solution was treated with a solution of 0.43 mL (2.1 eq.) of dry Et$_3$N and 0.12 mL (1.1 eq.) of ethanethiol in 20 mL of dry THF added dropwise to the reaction solution over a 2 hour period. The reaction solution darkened to a deep reddish brown. Stirring was maintained for about 65 hours. The excess TiCl$_4$ was neutralized by the addition of 5 mL of methanol. The solvents were then removed in vacuo yielding a yellow oil. The oil was chromatographed on silica gel using 5–20% ethyl acetate in hexane as eluent yielding 0.21 g of a colorless oil: $^1$H NMR (CDCl$_3$) δ 1.096 (t, 3H, J=7.2 Hz), 1.355 (s, 9H), 1.68–1.97 (m, 12H), 2.238 (q, 2H, J=7.2 Hz), 2.66 (br s, 1H), 3.59 (br s, 1H), 6.91–7.32 (m, 4H) ; $^{13}$C NMR (CDCl$_3$) δ 15.11, 25.89, 27.13, 28.04, 30.29, 35.48, 35.57, 36.96, 39.03, 39.36, 119.59, 120.41, 122.50, 126.66, 128.57, 141.44, 150.91, 153.22, 176.86.

(c) Synthesis of 4-ethylthio-4-(3-pivaloyloxyphenyl)spiro[1,2-dioxetane-3,2'-tricyclo[3.3.1.1$^{3,7}$]decane] (2). A small photooxygenation apparatus was charged with 60 mg (0.16 mmol) of the vinyl sulfide, 180 mg of polymer-bound Rose Bengal (U.S. Pat. No. 4,315,998), and 20 mL of CH$_2$Cl$_2$ dried over MgSO$_4$. The resulting mixture was then cooled to −78° C. with oxygen bubbling through it. After several minutes, the reaction solution was irradiated with a 1000 W sodium lamp for 25 min. TLC using 10% ethyl acetate in hexane showed conversion to a new material which emitted light when heated. The sensitizer was filtered off, the solvent evaporated at 0° C. and the material examined by $^1$H NMR. TLC suggested a higher degree of decomposition than was evident from the NMR spectrum suggesting that the dioxetane is less stable on silica. Mixing a sample of the dioxetane with an excess of TBAF in DMSO produced yellow chemiluminescence. $^1$H NMR (CDCl$_3$) δ 1.117 (t, 3H, J=7.2 Hz), 1.20–2.1 (m, 21H), 2.21 (br s, 1H), 2.27–2.40 (m, 2H), 3.11 (br s, 1H), 7.04–7.60 (m, 4H).

Example 3

Synthesis of Compound 3. 4-(p-Fluorophenylthio)-4-(3-hydroxyphenyl)spiro[1,2-dioxetane-3,2'-tricyclo[3.3.1.1$^{3,7}$]decane].

(a) Synthesis of [(3-hydroxyphenyl)-(p-fluorophenylthio)-methylene]tricyclo[3.3.1.1$^{3,7}$]decane. A solution of 10.33 g (40.3 mmol) of the hydroxy ketone of Example 1(a) and 250 mL of dry THF was purged with argon and treated with 9.8 mL (2.2 eq.) of TiCl$_4$. After 30 min, the resulting brown solution was treated with a solution of 25.0 mL (4.4 eq.) of dry Et$_3$N and 4.8 mL (1.1 eq.) of 4-fluorothiophenol in 200 mL of dry THF added dropwise to the reaction solution over a 2 hour period. The reaction solution darkened to a deep reddish brown while stirred over night. Dry Et$_3$N (100 ML) was added, changing the color to yellow. The excess TiCl$_4$ was neutralized by the addition of 2 mL of ethanol. The solvents were then removed in vacuo from the filtrate yielding a brownish yellow solid. This solid was then taken up into 500 mL of ethyl acetate and the resulting mixture washed several times with water (emulsion formed). The ethyl acetate layer was then dried over magnesium sulfate, filtered and concentrated in vacuo yielding a viscous yellow oil which smelled of the thiophenol. The oil was chromatographed on silica gel using methylene chloride as eluent. The vinyl sulfide was collected in two fractions, the first being contaminated with the thiophenol, the second being pure product. The first fraction was chromatographed on silica gel using 10–20% ethyl acetate in hexane as eluent yielding a second crop of vinyl sulfide which combined with the previous crop yielded 11.7 g: $^1$H NMR (CDCl$_3$) δ 1.75–2.05 (m, 12H), 2.783 (br s, 1H), 3.674 (br s, 1H), 4.559 (s, 1H), 6.57–7.118 (m, 8H).

(b) Synthesis of 4-(p-Fluorophenylthio)-4-(3-hydroxyphenyl)spiro[1,2-dioxetane-3,2'-tricyclo[3.3.1.1$^{3,7}$]decane] (3). A small photooxygenation apparatus was charged with 54 mg of the vinyl sulfide, 1–2 mg of methylene blue, 5 mL of CH$_2$Cl$_2$ (dried over MgSO$_4$) and 5 mL of CF$_3$CH$_2$OH. The resulting solution was then cooled to −40° C. with oxygen bubbling through it. After several minutes, the reaction solution was irradiated with a 1000 W sodium lamp for 24 min to produce the dioxetane as shown by the appearance of a new material by TLC which eluted immediately below the alkene and emitted light when heated.

Example 4

Synthesis of Compound 4. 4-(p-Fluorophenylthio)-4-(3-pivaloyloxyphenyl)spiro[1,2-dioxetane-3,2'tricyclo[3.3.1.1$^{3,7}$]decane].

(a) Synthesis of [(3-pivaloyloxyphenyl)-(p-fluorophenylthio)methylene]tricyclo[3.3.1.1$^{3,7}$]decane. The pivalate-protected ketone described in example 3 (a) was converted to the vinyl sulfide by stirring 0.63 g (1.85 mmol) of the ketone, 30 mL of dry THF and 0.22 mL (1.1 eq.) of TiCl$_4$. The resulting orange solution was stirred under argon for 5 minutes. A solution of 0.57 mL (2.2 eq.) of Et$_3$N and 0.22 mL (1.1 eq.) of p-fluorothiophenol in 30 mL of dry THF was then added dropwise to the reaction solution over 30 min while the reaction solution turned purple. Stirring was maintained for ca. 72 hours. The excess $TiCl_4$ was neutralized by the addition of ca. 2 mL of ethanol, the solvents evaporated and the residue purified by chromatography using 1–10% ethyl acetate in hexane. The alkene (0.35 g) was obtained as an oil: $^1$H NMR ($CDCl_3$) δ 1.330 (s, 9H), 1.70–2.05 (m, 12H), 2.775 (br s, 1H), 3.694 (br s, 1H), 6.78–7.20 (m, 8H).

(b) Synthesis of 4-(p-Fluorophenylthio)-4-(3-pivaloyloxyphenyl)spiro[1,2-dioxetane-3,2'tricyclo [3.3.1.1$^{3,7}$]decane] (4). A small photooxygenation apparatus was charged with 54 mg (0.12 mmol) of the vinyl sulfide, 150 mg of polymerbound Rose Bengal, and 25 mL of $CH_2Cl_2$ dried over $MgSO_4$. The resulting solution was then cooled to −78° C. with oxygen bubbling through it. After several minutes, the reaction mixture was irradiated with a 1000 W sodium lamp for 3.5 hours. TLC using 10% ethyl acetate in hexane showed conversion to a new material which emitted light when the plate was heated. The sensitizer was filtered off, the solvent evaporated and the material purified by chromatography oh silica with 20% ethyl acetate in hexane which yielded 30 mg of slightly yellow oil which emitted light when a sample was heated on a TLC plate and additionally produced red chemiluminescence when triggered with DMSO/TBAF. $^1$H NMR ($CDCl_3$) δ 1.375 (s, 9H), 1.68–1.97 (m, 12H), 2.66 (br s, 1H), 3.59 (br s, 1H), 6.74–7.95 (m, 8H).

Example 5

Synthesis of Comnound 5. 4-(2,2,2-trifluoroethylthio)-4-(3-hydroxyphenyl)spiro[1,2-dioxetane-3,2'-tricyclo[3.3.1.1$^{3,7}$] decane].

(a) Synthesis of [(3-hydroxyphenyl)(2,2,2-trifluoroethylthio)methylene]tricyclo[3.3.1.1$^{3,7}$]decane. An argon-purged round bottom flask was charged with 1.0 g (3.9 mmol) of the ketone of Example 2(a), 40 mL of anhydrous THF and 1.0 ML (2.3 eq.) of $TiCl_4$. The resulting brown solution was stirred under argon for 30 minutes at-room temperature. A solution of 2.4 mL (4.4 eq.) of triethylamine dry $Et_3N$ and 0.38 mL (1.1 eq.) of 2,2,2-trifluoroethanethiol in 60 mL of dry THF was then -added dropwise to the reaction solution over 1.5 hours while the reaction solution darkened to a deep reddish brown. Stirring was maintained overnight. A portion of dry $Et_3N$ (10 mL) was added to the reaction solution followed by 10 mL of methanol. The reaction mixture was allowed to stir for an hour and then suction filtered. The filtrate was evaporated yielding a gummy yellow solid. This solid was then taken up in $CH_2Cl_2$ and the resulting mixture washed with water (emulsion formed). The $CH_2Cl_2$ layer was then dried over $MgSO_4$, filtered and concentrated in vacuo yielding a yellow solid which smelled of thiol. The solid was chromatographed on silica gel using $CH_2Cl_2$ as eluent. The vinyl sulfide and the starting ketone were recovered. The solvents were removed in vacuo from the first eluted fraction yielding 0.16 g of light yellow oil. $^1$H NMR ($CDCl_3$) δ 1.65–2.02 (m, 12H), 2.624 (br s, 1H), 2.791 (q, 2H, J=9.8 Hz coupled to F), 3.609 (br s, 1H), 4.892 (s, 1H), 6.70–6.86 (m, 3H), 7.207 (t, 1H); $^{13}$C NMR ($CDCl_3$) δ 27.949, 33.899 (q, J=31 Hz), 35.901, 35.962, 36.842, 38.906, 39.240, 114.244, 116.611, 122.591, 125.70 (q, J=277 Hz), 129.420, 140.226, 155.190, 155.403.

(b) Synthesis of 4-(2,2,2-trifluoroethylthio)-4-(3-hydroxyphenyl)spiro[1,2-dioxetane-3,2'-tricyclo[3.3.1.1$^{3,7}$] decane] (5). A small photooxygenation apparatus was charged with 47.2 mg of the vinyl sulfide, 2 mg of methylene blue, and 20 mL of dry $CH_2Cl_2$. The resulting solution was then cooled to −78° C. with oxygen bubbling through it. After several minutes, the reaction solution was irradiated with a 1000 W sodium lamp for 45 min to produce mainly the dioxetane as shown by the light emitted on heating the TLC plate. The solution was concentrated and the product isolated by preparative TLC using 20% ethyl acetate in hexane yielding 30.4 mg of the product as a slightly yellow oil. Mixing a sample of the dioxetane with excess TBAF in DMSO produced orange-yellow light. $^1$H NMR ($CDCl_3$) δ 1.16–2.10 (m, 12H), 2.31 (br s, 1H), 2.948 (dq, 2H), 3.02 (br s, 1H), 5.35 (br s, 1H), 6.878 (dd, 1H), 7.14–7.38 (m, 3H).

TABLE 2

Alkoxy and Aryloxy Dioxetane Compounds

| Dioxetane | R | X |
|---|---|---|
| 6 | $CH_3$ | H |
| 7 | $CH(CH_3)_2$ | H |
| 8 | $CH_2CH=CH_2$ | H |
| 9 | $CH_2CH_2CN$ | H |
| 10 | $CH_2CH_2OH$ | H |
| 11 | $C_6H_5$ | H |
| 12 | $COCH_3$ | H |
| 13 | $CH_2CH_3$ | H |
| 14 | $CH(CF_3)_2$ | H |
| 15 | $CH_2CCl_3$ | H |
| 16 | $CH_2CHCl_2$ | H |
| 17 | $CH_2CF_2CF_3$ | H |
| 18 | $CH_2CF_2CF_2CF_3$ | H |
| 19 | 2,6-difluorophenyl | H |
| 20 | $CH_3$ | $COC(CH_3)_3$ |
| 21 | $CH_3$ | $Si(CH_3)_2$t-Bu |
| 22 | $CH_3$ | $SiPh_2$t-Bu |
| 23 | $CH_3$ | $PO(OCH_2CH_2CN)_2$ |
| 24 | $CH_3$ | $PO_3Na_2$ |

Example 6

Synthesis of Compound 6. 4-(3-Hydroxyphenyl)-4-methoxyspiro[1,2-dioxetane-3,2'-tricyclo[3.3.1.1$^{3,7}$] decane]. The vinyl sulfide of Example 1(b) (0.113 g) was irradiated for 15 min in 20 mL of methanol containing a few crystals (<1 mg) of methylene blue with continuous oxygen bubbling at −78° C. using a 1000 W Na lamp. Iodine (0.096 g) and 1 mL of 30% $H_2O_2$ were added and the mixture warmed to room temperature. Progress of the reaction was monitored by the disappearance of starting material by TLC (20% ethyl acetate in hexane) and the appearance of new bands which emitted blue light when the plate was heated and by observing the color of chemiluminescence from an aliquot of the reaction solution reacted with 0.1M TBAF in DMSO. The yellow emission of dioxetane 1 was gradually replaced by the blue emission of dioxetane 6 over a period of several hours. The solution was concentrated to 1–2 mL and separated on preparative TLC with 10% ethyl acetate in hexane. The band containing dioxetane 6 was collected, desorbed and evaporated yielding 77 mg.

Example 7

Alternate Synthesis of Compound 6. The vinyl sulfide of Example 1(b) (0.104 g) was irradiated for 23 min in 10 mL of $CH_2Cl_2$ containing a few crystals (<1 mg) of methylene blue with continuous oxygen bubbling at −78° C. using a 1000 W Na lamp. N-Chlorosuccinimide (42.8 mg) was added. After 10 min, 28 μL of methanol (2 eq.) was added and the solution warmed to room temperature. After an additional 30 min, TLC showed a new material which emitted blue light when the plate was heated. The solution was evaporated, the blue residue washed with ether and the ether evaporated to produce an oil. This oil was redissolved in a small amount of $CH_2Cl_2$. The product was separated by preparative TLC using 20% ethyl acetate in hexane yielding 50 mg of the product as a white solid.

Example 8

Synthesis of Compound 7. 4-Isopropoxy-4-(3-hydroxyphenyl)spiro[1,2-dioxetane-3,2'-tricyclo[3.3.1.1$^{3,7}$]decane]. The vinyl sulfide of Example 1(b) (0.131 g) was irradiated for 13 min in 20 mL of 2-propanol containing a few crystals (<1 mg) of methylene blue with continuous oxygen bubbling at −78° C. using a 1000 W Na lamp. Iodine (0.111 g) and 1 mL of 30% $H_2O_2$ were added and the mixture warmed to room temperature. Progress of the reaction was monitored by the appearance of a new material by TLC (40% ethyl acetate in hexane) which emitted blue light when the plate was heated and by observing the color of chemiluminescence from an aliquot of the reaction solution reacted with 0.1M TBAF in DMSO. The yellow emission of dioxetane 1 was gradually replaced by the blue emission of dioxetane 7 over a period of several hours. The solution was concentrated to 1–2 mL and separated on preparative TLC with 10% ethyl acetate in hexane. A band containing dioxetane 7 and adamantanone was collected, desorbed and evaporated yielding 24 mg of a white solid (Dioxetane 7): $^1$H NMR (CDCl$_3$) δ 1.160 (d), 1.257 (d), 1.22–2.14 (m), 3.08 (br s), 3.747 (sept), 5.641 (s), 6.892 (dd), 7.2 (br s), 7.25–7.33 (m).

A second component was also isolated as a pale yellow oil which exhibited an NMR spectrum consistent with the structure:

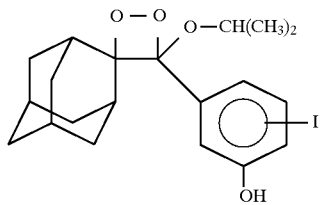

$^1$H NMR (CDCl$_3$) δ 1.145 (d), 1.253 (d), 1.20–2.14 (m), 3.06 (br s), 3.715 (sept), 5.77 (br s), 6.8–7.5 (m), 7.707 (d).

Example 9

Synthesis of Compound 8. 4-(3-Hydroxyphenyl)-4-(2-propenyloxy)spiro[1,2-dioxetane-3,2'-tricyclo[3.3.1.1$^{3,7}$]decane]. The vinyl sulfide of Example 1(b) (0.100 g) was irradiated in 20 ML of $CH_2Cl_2$ containing a few crystals (<1 mg) of methylene blue with continuous oxygen bubbling at −78° C. using a 1000 W Na lamp. TLC indicated that the vinyl sulfide was consumed after 10 min. N-Chlorosuccinimide (0.0446 g) was added and the mixture maintained at −78° C. for 15 minutes. Allyl alcohol (50 uL) was added and the solution warmed to room temperature. Progress of the reaction was monitored by the appearance of a new material by TLC (20% ethyl acetate in hexane) which emitted blue light when the plate was heated and by observing the color of chemiluminescence from an aliquot of the reaction solution reacted with 0.1M TBAF in DMSO. The yellow emission of dioxetane 1 was gradually replaced by the blue emission of dioxetane 8. The solution was concentrated to dryness and the residue extracted with ether. The ether was evaporated and the resulting residue chromatographed on a silica prep. TLC plate with 20% ethyl acetate in hexane. The major band contained 47 mg of dioxetane 8: $^1$H NMR (CDCl$_3$) δ 1.09 (m, 1H), 1.26 (m, 1H), 1.471 (dq, 1H), 1.51–1.96 (m, 9H), 2.195 (br s, 1H), 3.127 (br s, 1H), 3.72–3.82 (m, 1H), 4.02–4.12 (m, 1H), 5.14–5.22 (m, 1H), 5.32–5.44 (m, 2H, vinylic H and phenolic OH), 5.90–6.03 (m, 1H), 6.86–6.93 (m, 1H), 7.19 (br s, 2H), 7.26–7.34 (m, 1H).

Example 10

Synthesis of Compound 9. 4-(2-Cyanoethoxy)-4-(3-hydroxyphenyl)spiro[1,2-dioxetane-3,2'-tricyclo[3.3.1.1$^{3,7}$]decane]. The vinyl sulfide of Example 1(b) (0.052 g) was irradiated in 10 mL of $CH_2Cl_2$ containing a few crystals (<1 mg) of methylene blue with continuous oxygen bubbling at −78° C. using a 1000 W Na lamp for 10 min. N-Chlorosuccinimide (0.0229 g) was added and the mixture maintained at −78° C. for 15 minutes. 2-Cyanoethanol (25.8 uL) in 3 mL of dry $CH_2Cl_2$ was added and the solution warmed to room temperature. Progress of the reaction was monitored by the appearance of a new material by TLC (20% ethyl acetate in hexane) which emitted blue light when the plate was heated and by observing the color of chemiluminescence from an aliquot of the reaction solution reacted with 0.1M TBAF in DMSO. The yellow emission of dioxetane 1 was gradually replaced by the blue emission of dioxetane 9 over a period of 45 min. The solution was concentrated to dryness and the residue dissolved in a minimal amount of $CH_2Cl_2$ and purified by prep. TLC with 25% ethyl acetate in $CH_2Cl_2$; $^1$H NMR (CDCL$_3$) δ 1.01–1.11 (m, 1H), 1.23–1.32 (M, 1H), 1.45–1.94 (m, 10H), 2.23 (br s, 1H), 2.60–2.72 (m, 1H), 2.76–2.90 (m, 1H), 3.06 (br s, 1H), 3.49–3.60 (m, 1H), 3.69–3.81 (m, 1H), 5.93 (br s, 1H), 6.88–6.98 (m), 7.19 (br s, 2H), 7.325 (t, 1H).

Example 11

Synthesis of Compound 10. 4-(2-Hydroxyethoxy)-4-(3-hydroxyphenyl)spiro[1,2-dioxetane-3,2'-tricyclo[3.3.1.1$^{3,7}$]decane]. The vinyl sulfide of Example 1(b) (0.099 g) was irradiated for 11.5 min in 15 mL of $CH_2Cl_2$ containing a few crystals (<1 mg) of methylene blue with continuous oxygen bubbling at −78° C. using a 1000 W Na lamp. TLC indicated that the vinyl sulfide was consumed. N-Chlorosuccinimide (0.044 g) was added and the mixture maintained at −78° C. for 15 minutes. Ethylene glycol (37 uL) was added and the solution warmed to room temperature. Progress of the reaction was monitored by the appearance of a new material by TLC (20% ethyl acetate in hexane) which emitted blue light when the plate was heated and by observing the color of chemiluminescence from an aliquot of the reaction solution reacted with 0.1M TBAF in DMSO. The yellow emission of dioxetane 1 was gradually replaced by the blue emission of dioxetane 10 over a period of an hour. The solution was concentrated to dryness and the residue extracted with ether. The ether was evaporated and the resulting residue chromatographed on a silica prep. TLC plate with 40% ethyl acetate in hexane. The major band contained 18 mg of dioxetane 10.

Example 12

Synthesis of Compound 11. 4-(3-Hydroxyphenyl)-4-phenoxyspiro[1,2-dioxetane-3,2'-tricyclo[3.3.1.1$^{3,7}$]decane]. The vinyl sulfide of Example 1(b) (0.106 g) was irradiated for 10 min in 20 mL of $CH_2Cl_2$ containing a few crystals (<1 mg) of methylene blue with continuous oxygen bubbling at −78° C. using a 1000 W Na lamp. TLC indicated that the vinyl sulfide was consumed. N-Chlorosuccinimide (0.047 g) was added and the mixture maintained at −78° C. for 15 minutes. Phenol (83 mg) was added and the solution warmed to room temperature. Progress of the reaction was monitored by the appearance of a new material by TLC (20% ethyl acetate in hexane) which emitted blue light when the plate was heated and by observing the color of chemiluminescence from an aliquot of the reaction solution reacted with 0.1M TBAF in DMSO. The yellow emission of dioxetane 1 was gradually replaced by the blue emission of dioxetane 11 over a period of an hour. The solution was concentrated and the residue chromatographed on a silica prep. TLC plate with 20% ethyl acetate in hexane. The major band was isolated and found to contain a mixture of phenol, ca. 60 mg of dioxetane 11 and ca. 5 mg of adamantanone. Dioxetane 11: $^1$H NMR (CDCl$_3$) δ 1.09–1.19 (m), 1.25–1.35 (m), 1.45–1.54 (m), 1.56–2.14 (m), 2.26 (br s), 3.28 (br s), aromatic peaks could not be resolved from residual phenol.

Example 13

Synthesis of Compound 12. 4-Acetoxy-4-(3-hydroxyphenyl)spiro[1,2-dioxetane-3,2'-tricyclo[3.3.1.1$^{3,7}$]decane]. The vinyl sulfide of Example 1(b) (50 mg) was irradiated for 25 min in 20 mL of CH$_2$Cl$_2$ containing 2 mg of methylene blue with continuous oxygen bubbling at −78° C. using a 1000 W Na lamp. Mercuric acetate (400 mg) in 5 mL of 1,1,1,3,3,3-hexafluoro-2-propanol was added. TLC indicated the formation of two new products which emitted light upon heating the plate. The solution was evaporated, the blue residue was extracted with ether, the ether solution filtered and evaporated to a blue oil. The oil was redissolved in a small amount of CH$_2$Cl$_2$ and subjected to preparative TLC using 20% ethyl acetate in hexane. A band was isolated which contained 40 mg of dioxetane 12. A small quantity of dioxetane 14 was also obtained. Dioxetane 12: $^1$H NMR (CDCl$_3$) δ 1.06 (m, 1H), 1.27 (m, 1H), 1.48 (m, 1H), 1.54–1.90 (m, 9H), 2.193 (s, 3H), 2.26 (br s, 1H), 3.06 (br s, 1H), 5.66 (br s, 1H), 6.80 (m, 1H), 7.12 (br s, 2H), 7.248 (t, 1H).

Example 14

Synthesis of Compound 13. A small photooxygenation apparatus was charged with 99.1 mg of the vinyl sulfide of Example 3(a), 1–2 mg of methylene blue, 10 mL of CH$_2$Cl$_2$ and 10 mL of absolute ethanol. The resulting solution was then cooled to 0° C. with oxygen bubbling through it. After several minutes, the reaction solution was irradiated with a 1000 W sodium lamp for 15 min. NCS (40.0 mg, 1.1 eq.) was added, the reaction maintained at 0° C. for 60 min and then at room temperature for 3 h. The solvents were evaporated and the residue purified by preparative TLC, eluting with CH$_2$Cl$_2$. A colorless oil (47.6 mg) was produced. Dioxetane 13: $^1$H NMR (CDCl$_3$) δ 1.05–1.90 (m, 15H), 2.17 (br s, 1H), 3.09 (br s, 1H), 3.29 (m, 1H), 3.55 (m, 1H), 5.68 (br s, 1H), 6.86–7.36 (m, 4H).

Example 15

Synthesis of Compound 14. 4-(Hexafluoroisopropoxy)-4-(3-hydroxyphenyl)spiro[1,2-dioxetane-3,2'-tricyclo[3.3.1.1$^{3,7}$]decane]. The vinyl sulfide of Example 2(b) (0.102 g) was irradiated for 10 min in 20 mL of CH$_2$Cl$_2$ containing 2 mg of methylene blue with continuous oxygen bubbling at. −78° C. using a 1000 W Na lamp. The solution was poured into a solution of 5 mL of 1,1,1,3,3,3-hexafluoro-2-propanol in 10 mL of CH$_2$Cl$_2$. Mercuric acetate (ca. 50 mg) in 2 mL of hexafluoro-2-propanol was added gradually and the solution stirred for 30 min. TLC showed two new materials which emitted light when the plate was heated. The solution was evaporated, the blue residue washed with ether and the ether evaporated to produce an oil. This oil was redissolved in a small amount of CH$_2$Cl$_2$ and the product isolated by preparative TLC using 30% ethyl acetate in hexane yielding 8.1 mg of the product as a colorless oil. Reaction of a sample of the dioxetane with an excess of tetrabutylammonium fluoride in DMSO produced green chemiluminescence. $^1$H NMR (CDCl$_3$) δ 1.13 (m, 1H), 1.32 (m, 1H), 1.46–2.16 (m, 10H), 2.234 (br s, 1H), 2.994 (br s, 1H), 4.646 (br s, 1H), 5.326 (br s, 1H), 6.86–7.40 (m, 4H); $^{19}$F NMR (CDCl$_3$) δ (rel. to CFCl$_3$) −72.316, −72.013 (d).

Example 16

Synthesis of Compound 15. 4-(3-Hydroxyphenyl)-4-(2,2,2-trichloroethoxy)spiro[1,2-dibxetane-3,2'-tricyclo[3.3.1.1$^{3,7}$]decane]. The vinyl sulfide [(3-hydroxyphenyl) ethylthiomethylene]tricyclo[3.3.1.1$^{3,7}$]decane (102 mg) was irradiated for 20 min in 10 ML of CH$_2$Cl$_2$ containing 1 mg of methylene blue with continuous oxygen bubbling at −40° C. using a 1000 W Na lamp. N-Chlorosuccinimide (1 eq.) was added. After 10 min, 3 mL of 2,2,2-trichloroethanol was added and the solution warmed to room temperature. After an additional 30 min, TLC showed a new material which emitted blue-green light when the plate was heated. The solution was evaporated, redissolved in a small amount of CH$_3$OH and evaporated. The product was separated by preparative TLC using 20% ethyl acetate in hexane yielding 53.5 mg of the product as a slightly yellow oil which contained some decomposition products: $^1$H NMR (CDCl$_3$) δ 1.12 (m, 1H), 1.30 (m, 1H), 1.46–2.16 (m, 10H), 2.227 (br s, 1H), 3.198 (br s, 1H), 3.909 (d, 1H, J=10.3 Hz), 4.133 (d, 1H, J=10.3 Hz), 5.75 (br s, 1H), 6.940 (dd, 1H), 7.06–7.42 (m, 3H).

Example 17

Synthesis of Comoound 16. 4-(2,2-Dichloroethoxy)-4-(3-hydroxyphenyl)spiro[1,2-dioxetane-3,2'-tricyclo-[3.3.1.1$^{3,7}$]decane]. The vinyl sulfide [(3-hydroxyphenyl) ethylthiomethylene]tricyclo[3.3.1.1$^{3,7}$]decane (111 mg) was irradiated for 16 min in 10 mL of CH$_2$Cl$_2$ containing 1 mg of methylene blue with continuous oxygen bubbling at −78° C. using a 1000 W Na lamp. N-Chlorosuccinimide (50 mg, 1 eq.) was added. After 10 min, 60.7 μL of 2,2-dichloroethanol (2 eq.) was added and the solution warmed to room temperature. After an additional 30 min, TLC showed a new material which emitted blue-green light when the plate was heated. The solution was evaporated, redissolved in a small amount of CH$_2$Cl$_2$ and filtered. The product was separated by preparative TLC using 20% ethyl acetate in hexane yielding 45 mg of the product as a slightly yellow oil: $^1$H NMR (CDCl$_3$) δ 1.05 (m, 1H), 1.27 (m, 1H), 1.44–2.04 (m, 10H), 2.23 (br s, 1H), 3.098 (br s, 1H), 3.711 (dd, 1H, J=11, 7.7 Hz), 3.866 (dd, 1H, J=11, 4.4 Hz), 5.912 (dd, 1H, J=7.7, 4.4 Hz), 5.641 (br s, 1H), 6.929 (dd, 1H), 6.98–7.42 (m, 3H).

Example 18

Synthesis of Compound 17. 4-(3-Hydroxyphenyl)-4-(2,2,3,3,3-pentafluoropropoxy)spiro[1,2-dioxetane-3,2'-tricyclo [3.3.1.1$^{3,7}$]decane]. The vinyl sulfide of Example 2(b) (0.112 g) was irradiated for 10 min in CH$_2$Cl$_2$ containing methylene blue with continuous oxygen bubbling at −78° C. using a 1000 W Na lamp. The solution was poured into a solution of mercuric acetate (100 mg, 0.84 eq.) in 5 mL of 2,2,3,3,3-pentafluoro-1-propanol and stored at −13° C. over night. TLC indicated the formation of two new products, both of which emitted light on heating. The solution was evaporated, the blue residue washed with ether and the ether evaporated to produce an oil. This oil was redissolved in a small amount of $CH_2Cl_2$ and the product isolated by preparative TLC using 30% ethyl acetate in hexane yielding 41.2 mg of dioxetane 17 as a colorless oil in addition to some of the acetoxy-substituted dioxetane (12); dioxetane 17: $^1$H NMR (CDCl$_3$) δ 1.04 (m, 1H), 1.28 (m, 1H), 1.46–2.14 (m, 10H), 2.23 (br s, 1H), 3.017 (br s, 1H), 3.658 (m, 1H), 4.006 (m, 1H), 5.13 (s, 1H), 6.93 (dd, 1H), 6.98–7.28 (br s, 2H), 7.338 (t, 1H).

Example 19

Synthesis of Compound 18. 4-(2,2,3,3,4,4,4-Heptafluorobutoxy)-4-(3-hydroxyphenyl)spiro[1,2-dioxetane-3,2'-tricyclo[3.3.1.1$^{3,7}$]decane]. The vinyl sulfide of Example 2(b) (0.100 g) was irradiated for 10 min in 20 mL of $CH_2Cl_2$ containing 2 mg of methylene blue with continuous oxygen bubbling at −78° C. using a 1000 W Na lamp. The solution was poured into a solution of mercuric acetate (100 mg, 0.95 eq.) in 5 mL of 2,2,3,3,4,4,4-heptafluoro-1-butanol. After one hour, TLC indicated the formation of two new products, both of which emitted light on heating. The solution was evaporated, the blue residue washed with ether and the ether evaporated to produce an oil. This oil was redissolved in a small amount of $CH_2Cl_2$ and the product isolated by preparative TLC using 30% ethyl acetate in hexane yielding 26.3 mg of dioxetane 18 as a colorless oil in addition to some of the acetoxy-substituted dioxetane 12; dioxetane 18: $^1$H NMR (CDCl$_3$) δ 1.05 (m, 1H), 1.28 (m, 1H), 1.45–1.96 (m, 10H), 2.24 (br s, 1H), 3.029 (br s, 1H), 3.71 (m, 1H), 4.04 (m, 1H), 5.332 (br s, 1H), 6.935 (dd, 1H), 6.98–7.52 (br s, 2H), 7.338 (t, 1H); $^{19}$F NMR (CDCl$_3$) δ −127.65, −120.58, −120.55, −120.52, −120.48, −120.46, −81.40, −81.36, −81.33.

Example 20

Synthesis of Compound 19. 4-(2',6'-Difluorophenoxy)-4-(3-hydroxyphenyl)spiro[1,2-dioxetane-3,2'-tricyclo[3.3.1.1$^{3,7}$]decane]. The vinyl sulfide of Example 2(b) (0.100 g) was irradiated for 10 min in 20 mL of $CH_2Cl_2$ containing 2 mg of methylene blue with continuous oxygen bubbling at −40° C. using a 1000 W Na lamp. NCS (44.7 mg, 1 eq.) was added followed after 15 min by 100 mg (2.3 eq.) of 2,6-difluorophenol in 3 ML of $CH_2Cl_2$. The solution was allowed to warm to room temperature. After an hour, TLC showed a new material which emitted blue-green light when the plate was heated. The solution was evaporated, redissolved in a small amount of $CH_2Cl_2$ and the product isolated by two successive preparative TLC purifications first using 5–20% ethyl acetate in hexane and then using $CH_2Cl_2$ on a second plate yielding 11.2 mg of the product as a slightly yellow oil; $^1$H NMR (CDCl$_3$) δ 1.29–2.24 (m, 13H), 3.31 (br s, 1H), 5.00 (m, 1H), 6.68–7.6 (m, 7H).

Example 21

Synthesis of Compound 20. 4-Methoxy-4-(3-pivaloyloxyphenyl)spiro[1,2-dioxetane-3,2'-tricyclo[3.3.1.1$^{3,7}$]decane]. The vinyl sulfide of Example 4(a) (0.051 g) was irradiated in 20 mL of $CH_3OH$ containing ca. 1 mg of Rose Bengal with continuous oxygen bubbling at −78° C. using a 1000 W Na lamp. When the alkene was shown by TLC to be completely consumed, iodine (0.096 g) and 1 mL of 30% $H_2O_2$ were added and the mixture warmed to room temperature. Progress of the reaction was monitored by the disappearance of dioxetane 4 by TLC (20% ethyl acetate in hexane) and the appearance of new bands which emitted blue light when the plate was heated and by observing the color of chemiluminescence from an aliquot of the reaction solution reacted with 0.1M TBAF in DMSO. The yellow emission of dioxetane 4 was gradually replaced by the blue emission of dioxetane 20 over a period of two hours. The solution was concentrated to 1–2 mL and separated on preparative TLC with 5% ethyl acetate in hexane. The band containing dioxetane 20 was collected and desorbed and evaporated to yield the product as a slightly yellow oil: $^1$H NMR (CDCl$_3$) δ 1.02 (m, 1H), 1.28 (m, 1H), 1.375 (s, 9H), 1.45–1.94 (m, 10H), 2.17 (br s, 1H), 3.04 (br s, 1H), 3.232 (s, 3H), 7.07–7.49 (m, 4H).

Example 22

Synthesis of Compound 21. 4-(3-t-Butyldimethylsilyloxyphenyl)-4-methoxyspiro[1,2-dioxetane-3,2'-tricyclo-[3.3.1.1$^{3,7}$]decane]. This example demonstrates the interconversion of triggerable dioxetanes by replacing one protecting group with another. A 152 mg portion (1 mmol) of t-butyldimethylsilyl chloride was added to a solution of imidazole (69 mg, 1 mmol) in 2 mL of $CH_2Cl_2$ causing formation of a white precipitate. The mixture was filtered and the supernatant transferred into a solution containing 285 mg (0.94 mmol) of dioxetane 6 in 1 mL of $CH_2Cl_2$. After standing for 1 h, the solution was filtered, washed with 2×1 mL of water, dried and evaporated. The residue was dissolved in hexane, filtered and evaporated producing 310 mg of dioxetane 21 as an oil which produced blue chemiluminescence on heating or addition to a solution of 0.1M TBAF in DMSO. $^1$H NMR were identical to those reported for this compound in U.S. Pat. No. 4,857,652.

Example 23

Synthesis of Compound 22. 4-(3-t-Butyldiphenylsilyloxyphenyl)-4-methoxyspiro[1,2-dioxetane-3,2'-tricyclo-[3.3.1.1$^{3,7}$]decane]. This example further demonstrates the interconversion of triggerable dioxetanes. A 950 mg portion (3.45 mmol) of t-butyldiphenylsilyl chloride was added to a solution of imidazole (236 mg, 3.47 mmol) in 25 mL of $CH_2Cl_2$ causing formation of a white precipitate. The mixture was filtered and 0.99 g (3.3 mmol) of dioxetane 6 was added to the supernatant. After stirring over night, the solution was filtered, washed with 3×20 mL of water, dried and evaporated. The residue was dissolved in hexane, washed with water, dried and allowed to crystallize at 4° C. Dioxetane 22 (767 mg) was obtained which produced blue chemiluminescence on heating or addition to a solution of 0.1M TBAF in DMSO. $^1$H NMR (CDCl$_3$) δ 0.75–0.82 (m, 1H), 1.10 (s, 9H), 1.35–1.87 (m, 11H), 2.03 (br s, 1H), 2.85 (br s, 4H), 6.9–7.75 (m, 14H).

Example 24

Synthesis of Compound 23. 4-(Methoxy)-4-(3-bis-(cyanoethyl)phosphoryloxyphenyl)spiro[1,2-dioxetane-3,2'-tricyclo[3.3.1.1$^{3,7}$]decane]. Examples 24 and 25 further demonstrate the interconversion of triggerable dioxetanes. A solution of anhydrous pyridine (3.0 mL, 37 mmol) in 10 mL of $CH_2Cl_2$ was placed under argon and cooled to 0° C. POCl$_3$ (1.608 g, 10.5 mmol) was added and the solution stirred for 15 min to cool. A solution of dioxetane 6 (1.006 g, 3.3 mmol) and pyridine (3.0 mL) in 10 mL of $CH_2Cl_2$ was added dropwise. The ice bath was removed and the reaction continued as the solution warmed to room temperature. TLC (3:1 ethyl acetate/hexane) showed complete conversion of dioxetane 6 in 90 min. A solution of 2-cyanoethanol (2.2 mL, 32 mmol) and 3.0 mL of pyridine was added and stirring maintained over night. The solution was evaporated to dryness yielding a white solid which was purified by chromatography on silica with 30–75% ethyl acetate in hexane yielding dioxetane 23 as a slightly yellow oil (1.24 g): $^1$H NMR (CDCl$_3$) δ 0.97 (d, 1H), 1.46–1.89 (m, 11H), 2.103 (br s, 1H), 2.819 (t, 4H), 3.039 (br s, 1H), 3.224 (s, 3H), 4.32–4.50 (m, 4H), 7.30–7.60 (m, 4H); $^{13}$C NMR (CDCl$_3$) δ 19.329, 19.420, 25.521, 25.642, 31.197, 31.379, 31.925, 32.593, 32.836, 34.414, 35.932, 49.773, 62.825, 62.916, 95.121, 111.057, 116.156, 120.648, 120.709, 129.724, 136.948, 149.757, 149.848; $^{31}$P NMR (CDCl$_3$) δ 9.45 (m) rel to ext. H$_3$PO$_4$.

Example 25
Synthesis of Compound 24. 4-(Methoxy)-4-(3-phosphoryloxyphenyl)spiro[1,2-dioxetane-3,2'-tricyclo-[3.3.1.1$^{3,7}$]decane], disodium salt. To a solution of dioxetane 23 (1.24 g, 2.54 mmol) dissolved in 50 mL of methanol was added a solution of 1.627 g (15.35 mmol) of sodium carbonate in 10 mL of Type I water (Lumigen, Southfield, Mich.). After stirring for 2 days, TLC using 30% methanol in CH$_2$Cl$_2$ showed complete removal of the cyanoethyl groups. The solid material was filtered off and washed with 50 mL of methanol. The methanol washes and reaction solution were combined and evaporated under reduced pressure yielding a white solid. The solid was freed of impurities by again dissolving in methanol, filtering and evaporating the methanol and crystallizing from methanol/acetone yielding 0.986 g of white solid which was identical by $^1$H NMR to an authentic sample (see U.S. Pat. No. 5,004,565).

Example 26
Alternate Synthesis of Vinyl Sulfide from Example 1(b) by Ti-Mediated Coupling (a) Synthesis of ethyl 3-methoxythiobenzoate. To an ice cooled solution of m-anisoyl chloride (8.53 g) in 10 ml of CH$_2$Cl$_2$ was added 4.85 mL of pyridine. After 10 min, ethanethiol (3.73 g) was added dropwise and the resulting solution stirred over night. The solution was diluted with 100 mL of methylene chloride, washed with saturated sodium bicarbonate then washed several times with water and dried. The thioester was obtained by evaporation of the solvent; 1H NMR (CDCl$_3$) δ 1.35 (t, 3H), 3.06 (q, 2H), 3.85 (s, 3H), 7.11–7.56 (m, 4H); $^{13}$C NMR (CDCl$_3$) δ 14.76, 23.53, 55.46, 111.43, 119.69, 119.78, 129.58, 138.60, 159.76, 192.02.
(b)Synthesis of [(3-methoxyphenyl)(ethylthio)methylene] tricyclo[3.3.1.13,7]decane. A three neck flask was purged with argon and charged with 100 mL of anhydrous THF. The flask was cooled in an ice bath and titanium trichloride (14.19 g) was added with stirring. Lithium aluminum hydride (LAH) (1.75 g) was added in small portions causing a brief exothermic reaction. After all of the LAH was added, the cooling bath was removed and triethylamine (12.6 mL) was added. The black mixture was refluxed for 100 min under argon and then cooled for 10 min. A solution of adamantanone (3.46 g) and ethyl 3-methoxythiobenzoate (1.5 g) in 50 mL of dry THF was added dropwise over 20 min. Reaction progress was monitored by TLC with 20% ethyl acetate in hexane. The crude reaction mixture was cooled to room temperature after 120 min, diluted with hexane and decanted. The residue was washed several times using a total of ca. 500 mL of hexane. The combined hexane solutions were filtered and evaporated leaving an oil. The alkene was purified by subjecting the oil to prep. TLC (15% ethyl acetate/hexane; $^1$H NMR (CDCl$_3$) δ 1.09–1.14 (t, 3H), 1.75–1.98 (m, 12H), 2.21–2.28 (q, 3H), 2.66 (s, 1H), 3.60 (s, 1H), 3.82 (s, 3H), 6.78–7.23 (m, 4H); $^{13}$C NMR (CDCl$_3$) δ 15.21, 25.96, 28.17, 28.48, 32.45, 35.45, 35.73, 37.07, 37.25, 39.10, 39.46, 39.98, 55.19, 112.04, 115.01, 121.08, 122.06, 128.85, 141.57, 152.62, 159.36.
(c) Synthesis of [(3-hydroxyphenyl)ethylthiomethylene] tricyclo-[3.3.1.1$^{3,7}$]decane. A solution of the vinyl sulfide from step (b) dissolved in dry DMF is added to a solution of sodium ethanethiolate in dry DMF under an atmosphere of argon. The mixture is refluxed for 3 hours or until TLC indicates cleavage of the methyl ether. The mixture is cooled to room temperature and carefully neutralized with dilute acid. The aqueous solution is extracted with ethyl acetate, the ethyl acetate washed with water, dried and evaporated. The residual product is purified by column chromatography.

Example 27
Comparison of Rates of Base-Induced Decay of Hydroxyphenyl Alkoxy or Aryloxy Dioxetanes. The first order decay of chemiluminescence of dioxetanes 14–19 in 0.2M 2-methyl-2-amino-1-propanol (221) buffer, pH 9.6 containing 0.88 mM Mg$^{+2}$ and 1.0 mg/mL of 1-trioctylphosphoniummethyl-4-tributylphosphoniummethylbenzene dichloride was measured at 37° C. in a Turner Designs (Sunnyvale, Calif.) model TD-20e luminometer. The half-lives of decay of chemiluminescence ($t_{1/2}$) of hydroxy-dioxetanes correlate with the times required to reach the maximum light intensity ($I_{max}$) in the alkaline phosphatase-triggered decomposition of the corresponding phosphate-dioxetanes under the same conditions. The half-life of decay of luminescence of the hydroxy dioxetane is, therefore, useful for predicting the grow-in kinetics of light emission for phosphatase triggering of phosphate dioxetanes; i.e. a fast $t_{1/2}$ for the hydroxy dioxetane indicates that the corresponding phosphate dioxetane is expected to reach $I_{max}$ more quickly. It is expected that, for example, the phosphate derivatives of dioxetanes 14–19 as well as others which can be produced by the process described herein will be useful in alkaline phosphatase-linked assays known in the art.

TABLE 3

Kinetics of Light Emission from Hydroxy Dioxetanes Prepared by the Process of the Present Invention.

| Dioxetane | $t_{1/2}$ (min) 37° C. |
|---|---|
| 14 | 0.16 |
| 15 | 3.7 |
| 16 | 4.1 |
| 17 | 3.4 |
| 18 | 4.9 |
| 19 | 1.76 |

Example 28
Comparison of Rates of Base-Induced Decay of a Hydroxyphenyl Alkylthio Dioxetane. The first order decay of chemiluminescence of dioxetane 3 in 0.2M 221 buffer, pH 9.6 containing 0.88 mM Mg$^{+2}$ and the surfactant enhancers shown below was measured at ambient temperature. Surfactant A is CTAB, B is poly (vinylbenzyltributylphosphonium chloride), C is poly (vinylbenzyltributylphosphonium chloride)-co-poly (vinylbenzyltrioctylphosphonium chloride), D is 1-trioctylphosphoniummethyl-4-tributylphosphoniummethylbenzene dichloride.
The results indicate the surprising discovery that the sulfur-substituted dioxetane exhibits kinetics for light emission comparable to dioxetane 6 in buffer.

TABLE 4

Kinetics of Light Emission from Dioxetane 3 in the Presence of Surfactants.

| Surfactant | Concentration | $t_{1/2}$ (min) |
|---|---|---|
| A | 0.41 g/L | 11.2 |
| B | 0.5 g/L | 4.2 |
| C | 0.5 g/L | 2.9 |
| D | 1.0 g/L | 2.0 |

Example 29

Fluoride Induced Chemiluminescence of Alkoxy and Aryloxy-Dioxetanes. A portion of each of the purified dioxetanes 6–23 was separately mixed with a solution of 0.1M tetrabutylammonium fluoride (TBAF) in DMSO causing a brief flash of blue-green light which could be seen in a darkened room by eye. Chemiluminescence persisted for several seconds. Light emission produced in this manner could also be produced with the dioxetane deposited on a silica gel TLC plate.

Example 30

Fluoride Induced Chemiluminescence from Sulfur-Substituted Dioxetanes. A portion of each of the dioxetanes 1–5 was separately mixed with a solution of 0.1M TBAF in DMSO causing a brief flash of yellow to reddish light which could be seen in a darkened room by eye. Chemiluminescence persisted for several seconds.

We claim:

1. A vinyl sulfide compound of the formula:

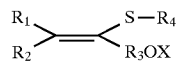

wherein $R_4$ is an organic group containing 1 to 20 carbon atoms and optionally heteroatoms, wherein $R_1$ and $R_2$ are selected from branched chain alkyl, and cycloalkyl groups which can optionally be joined together to form a cyclic or polycyclic group, wherein $R_3$ is selected from aryl, biaryl, heteroaryl, fused ring polycyclic aryl and fused ring polycyclic heteroaryl groups which can include additional substituents and wherein X is a protecting group which can be removed by an activating agent.

2. A vinyl sulfide compound of the formula:

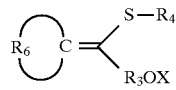

wherein $R_4$ is an organic group containing 1 to 20 carbon atoms and optionally heteroatoms, wherein

is a polycyclic alkyl group and which can optionally be substituted, wherein $R_3$ is selected from aryl, biaryl, heteroaryl, fused ring polycyclic aryl and fused ring polycyclic heteroaryl groups which can include additional substituents and wherein X is a protecting group which can be removed by an activating agent.

3. The compound of claim 2 wherein $R_4$ is selected from the group consisting of alkyl containing 1 to 12 carbon atoms which may be substituted with at least one halogen atom and aryl containing 6 to 20 carbon atoms which may be substituted with at least one halogen atom.

4. The compound of claim 2 wherein

is selected from the group consisting of substituted and unsubstituted adamantyl groups.

5. The compound of claim 2 wherein $R_3$ is a meta-phenyl group and wherein OX is selected from the group consisting of hydroxyl, alkoxy, substituted alkoxy, acyloxy having the formula $OOCR_{10}$ wherein $R_{10}$ is selected from alkyl and aryl groups containing 2 to 20 carbon atoms, trialkylsilyloxy, triarylsilyloxy, aryldialkylsilyloxy, OPO$(OR_8)_2$ wherein $R_8$ is an organic group, β-D-galactosyloxy and β-D-glucuronidyloxy groups.

6. The compound of claim 2 having the formula:

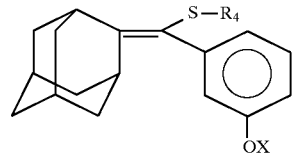

7. A compound having the formula:

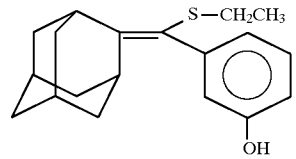

8. A compound having the formula:

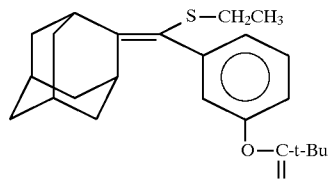

9. A compound having the formula:

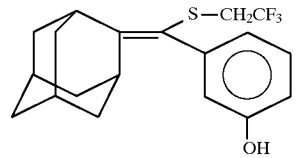

10. A compound having the formula:

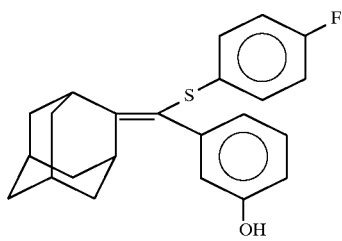

11. A compound having the formula:

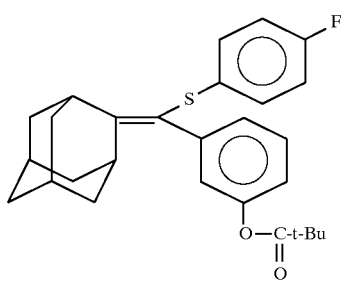

12. A process for producing a vinyl sulfide compound of the formula:

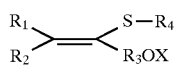

comprising reacting a ketone compound of the formula:

wherein $R_1$ and $R_2$ are organic groups which can optionally be joined together to form a cyclic or polycyclic group, with a thioester compound of the formula:

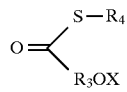

wherein $R_3$ is selected from aryl, biaryl, heteroaryl, fused ring polycyclic aryl and fused ring polycyclic heteroaryl groups which can optionally be substituted and wherein X is a protecting group which can be removed by an activating agent, wherein $R_4$ is an organic group containing 1 to 20 carbon atoms and optionally heteroatoms, in an aprotic organic solvent in the presence of a metallic reducing agent, a titanium salt and, optionally, an amine base to produce the vinyl sulfide.

13. A process for producing a vinyl sulfide compound of the formula:

comprising reacting a ketone compound of the formula:

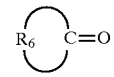

wherein

is a polycyclic alkyl group which can optionally be substituted with a thioester compound of the formula:

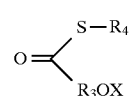

wherein $R_3$ is selected from aryl, biaryl, heteroaryl, fused ring polycyclic aryl and fused ring polycyclic heteroaryl groups which can optionally be substituted, wherein X is a protecting group which can be removed by an activating agent, and wherein $R_4$ is an organic group containing 1 to 20 carbon atoms and optionally heteroatoms, in an aprotic organic solvent in the presence of a metallic reducing agent, a titanium salt and, optionally, an amine base to produce the vinyl sulfide.

14. The process of claim 12 or claim 13 wherein the titanium salt is selected from the group consisting of titanium trichloride and titanium tetrachloride.

15. The process of claim 12 or claim 13 wherein the metallic reducing agent is lithium aluminum hydride and wherein an amine base is used.

* * * * *